United States Patent
Koehler

(10) Patent No.: US 10,973,483 B2
(45) Date of Patent: Apr. 13, 2021

(54) PHASE-CONTRAST AND DARK-FIELD CT RECONSTRUCTION ALGORITHM

(71) Applicant: KONINKLIJKE PHILIPS N.V., Eindhoven (NL)

(72) Inventor: Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 48 days.

(21) Appl. No.: 16/329,792

(22) PCT Filed: Sep. 7, 2017

(86) PCT No.: PCT/EP2017/072463
§ 371 (c)(1),
(2) Date: Mar. 1, 2019

(87) PCT Pub. No.: WO2018/046600
PCT Pub. Date: Mar. 15, 2018

(65) Prior Publication Data
US 2019/0192098 A1 Jun. 27, 2019

(30) Foreign Application Priority Data
Sep. 8, 2016 (EP) .................................. 16187830

(51) Int. Cl.
*A61B 6/00* (2006.01)
*G06T 11/00* (2006.01)
*A61B 6/03* (2006.01)

(52) U.S. Cl.
CPC ............ *A61B 6/5205* (2013.01); *A61B 6/032* (2013.01); *A61B 6/4291* (2013.01); *A61B 6/484* (2013.01);
(Continued)

(58) Field of Classification Search
CPC ..... A61B 6/5205; A61B 6/032; A61B 6/4291; A61B 6/484; G06T 11/006;
(Continued)

(56) References Cited

U.S. PATENT DOCUMENTS

2010/0091936 A1 4/2010 David
2012/0307966 A1 12/2012 Roessl
(Continued)

FOREIGN PATENT DOCUMENTS

WO 2013/171657 11/2013
WO 2016023782 2/2016
WO 2016207423 12/2016

OTHER PUBLICATIONS

Brendel, et al.: "Intensity-Based Iterative Reconstruction for Differential Phase-Contrast Imaging with Reconstruction Parameter Estimation", 13th International Meeting on Fully 3D Image Reconstruction in Radiology and Nuclear Medicine, May 21, 2015.
(Continued)

*Primary Examiner* — Jon Chang
(74) *Attorney, Agent, or Firm* — Larry Liberchuck

(57) ABSTRACT

A system and related method for signal processing. Interferometric projection data reconstructed into one or more images for a spatial distribution of a physical property of an imaged object. The interferometric projection data is derived from signals acquired by an X-ray detector (D), said signals caused by X-ray radiation after interaction of said X-ray radiation with an interferometer and with the object (OB) to be imaged, said interferometer (IF) having an inter-grating distance. The reconstructor (RECON) configured to perform, based on the projection data and a forward signal model, a reconstruction operation for one or more images in an image domain of a spatial distribution of at least one physical property of said object (OB) including a refractive index, wherein the reconstructor is configured to perform in
(Continued)

the reconstruction operation a scaling operation based on the inter-grating distance of the interferometer and/or on a distance of a location in said image domain from said interferometer (IF).

12 Claims, 7 Drawing Sheets

(52) U.S. Cl.
CPC .......... G06T 11/003 (2013.01); G06T 11/006 (2013.01); *G06T 2211/424* (2013.01)

(58) Field of Classification Search
CPC ............. G06T 2211/424; G06T 11/003; G06T 2207/10081; G06T 2211/40
See application file for complete search history.

(56) References Cited

U.S. PATENT DOCUMENTS

| | | | |
|---|---|---|---|
| 2014/0169524 A1 | 6/2014 | Sperl | |
| 2014/0226785 A1 | 8/2014 | Stutman | |
| 2014/0286475 A1* | 9/2014 | Nakamura | G01T 1/16 378/51 |
| 2015/0124927 A1* | 5/2015 | Koehler | G01N 23/201 378/19 |

OTHER PUBLICATIONS

Donath, et al.: "Inverse geometry for grating-based x-ray phase-contrast imaging", J. Appl. Phys. 106, 054703 (2009).

Yaroshenko, et al.: "Non-binary phase gratings for x-ray imaging with a compact Talbot interferometer", Optics Express, vol. 22, No. 1 (2014), pp. 548-556.

Ritter, et al.: "Simultaneous maximum-likelihood reconstruction for X-ray grating based phase-contrast tomography avoiding intermediate phase retrieval", Physics Med, Jul. 30, 2013.

Peter M. Joseph: "An Improved Algorithm for Reprojecting Rays through Pixel Images" in IEEE Transactions on Medical Imaging, vol. 1, Issue 3, pp. 192-196 (1982).

Bippus, et al.: "Projector and Backprojector for Iterative CT Reconstruction with Blobs using CUDA", 11th Fully 3D conference, Potsdam, Jul. 11-15, 2011, conference proceedings, pp. 68-71.

Koehler, et al.: "Iterative reconstruction for differential phase contrast imaging using spherically symmetric basis functions", Med. Phys, 38(8), 4542, 2011.

Zanette, et al.: "Trimodal low-dose X-ray tomography", PNAS 109(26), 10199 (2012).

* cited by examiner

A)

B)

PHASE-CONTRAST AND DARK-FIELD CT RECONSTRUCTION ALGORITHM

CROSS REFERENCE TO RELATED APPLICATIONS

This application is the U.S. National Phase application under 35 U.S.C. § 371 of International Application No. PCT/EP2017/072463 filed Sep. 7, 2017, published as WO 2018/046600 on Mar. 15, 2018, which claims the benefit of European Patent Application Number 16187830.1 filed Sep. 8, 2016. These applications are hereby incorporated by reference herein.

FIELD

The present disclosure relates to a signal processing system, to a signal processing method, to an imaging arrangement, to a computer program product, and to a computer readable medium.

BACKGROUND

Grating-based differential phase-contrast imaging is an emerging and promising approach to improve X-ray computed tomography. In addition to the spatial distribution of the linear attenuation coefficient, this method provides access to the spatial distribution of the electron density (which is essentially equivalent to the refraction index distribution) and of the small-angle scattering power of the object.

Grating based phase contrast imaging requires a grating interferometer. Different interferometer designs are discussed by Donath et al in "Inverse geometry for grating-based x-ray phase-contrast imaging", J. Appl. Phys. 106, 054703 (2009).

A reconstruction scheme for grating based tomography is described in Applicant's WO 2013/171657.

SUMMARY

There may therefore be a need in the art for an alternative image processing method or related system.

The object of the present disclosure is solved by the subject matter of the independent claims where further embodiments are incorporated in the dependent claims.

It should be noted that the following described aspect of the present disclosure equally applies to the image processing method, to the imaging arrangement, to the computer program product, and to the computer readable medium.

According to a first aspect of the present disclosure, there is provided a signal processing system, comprising:

an input port for receiving interferometric projection data derived from signals acquired by an X-ray detector of an interferometric X-ray imaging apparatus, said signals caused by X-ray radiation after interaction of said X-ray radiation with an interferometer and with an object to be imaged, said interferometer having an inter-grating distance;

a reconstructor configured to perform, based on the projection data and a forward signal model, a reconstruction operation for one or more images in an image domain of a spatial distribution of at least one physical property of said object including a refractive index, wherein the reconstructor is configured to perform in the reconstruction operation a scaling operation based on the inter-grating distance of the interferometer and/or on a distance of a location in said image domain from said interferometer; and an output port for outputting said one or more images.

According to one embodiment, the interferometer includes a source grating and said inter-grating distance corresponds to a distance between said source grating and a further grating of the interferometer.

According to one embodiment, the scaling operation further depends on a distance between the source grating and the detector.

According to one embodiment, said interferometer inter-grating distance corresponds to a distance between two gratings of the interferometer.

According to one embodiment, the distance between the image domain location and the interferometer corresponds to the distance between said image domain location and the source grating.

According to one embodiment, said distance between the image domain location and the interferometer corresponds to the distance between said image domain location and the or a one further grating of the interferometer.

According to one embodiment, the projection data has been acquired from different projection directions. In particular, the imaging apparatus is a CT scanner or a C-arm imaging apparatus, or any other. However, in other, alternative embodiments, the projection data is acquired along a single projection direction such as in classical radiography or in other applications such as bagging screening or other.

According to one embodiment the reconstructor is configured to fit said interferometric projection data to the signal model by adapting a plurality of fitting variables, said fitting variables including i) the one or more imaging variables for the one or more images and ii), in addition to said one or more imaging variables, a dedicated phase variable ($\psi$) for a fluctuation of said reference phase.

According to a further aspect there is provided a signal processing method, comprising the steps of;

receiving interferometric projection data derived from signals acquired by an X-ray detector of an interferometric X-ray imaging apparatus, said signals caused by X-ray radiation after interaction of said X-ray radiation with an interferometer and with an object to be imaged, said interferometer having an inter-grating distance;

performing, based on the projection data, a reconstruction operation for one or more images in an image domain of a spatial distribution of at least one physical property of said object including a refractive index, wherein the reconstructor is configured to perform in the reconstruction operation a scaling operation based on the inter-grating distance of the interferometer and/or on a distance of a location in said image domain from said interferometer; and outputting said one or more images.

According to one embodiment said physical property further includes any one or more of the following: i) attenuation, or ii) small angle scattering.

Specifically, the scaling operation is performed during forward projection operations through the image domain on (intermediate) images generated by the iterative reconstruction operation during the course of one or more iterations. The inter-grating distance of the interferometer relates to one or more distances between gratings of the interferometer. This signal processing system may be used in tomographic reconstruction of phase contrast and/or dark field imaging. The system takes into account in particular the effect that the phase contrast signal generated by an imaged object depends on its position along a projection ray. The proposed signal processing system employs a more accurate forward projection operator (also referred to herein as the forward signal model). In particular, magnification effect can be more accurately modelled by the scale factors because distances in relation to the interferometer are taken into account for the phase contrast signal channel. This results in more accurate reconstruction in particular for dark-field and phase contrast imagery.

In another embodiment, the signal processing system is further configured to take into account certain types of fluctuations in relation to the interferometer. Specifically, the reconstructor is further configured to reconstruct one or more images of a spatial distribution of one or more physical properties of said object, the reconstructor configured to fit said interferometric projection data to the forward signal model by adapting a plurality of fitting variables, said fitting variables including i) one or more imaging variables for the one or more images and ii), in addition to said one or more imaging variables, a dedicated phase variable for a fluctuation of said reference phase The physical properties of main interest herein are attenuation, refraction, and small angle scattering. The latter has been found to relate to micro-structures in the imaged object.

According to one embodiment, the projection data has been acquired from different projection directions such as in CT or tomosynthesis.

The fluctuation or "offset" of the reference phase can be modelled spatially and/or temporally.

Specifically, according to one embodiment, the reference phase fluctuation is modelled by said phase variable as a constant offset independent of said different projection directions.

According to one embodiment, the reference phase fluctuation is modeled by said phase variable as a non-constant offset that depends on said different projection directions.

According to one embodiment, the reference phase fluctuation is modeled by said phase variable to depend on a position of a detector element of said X-ray detector. Said differently, the reference phase fluctuation is modeled by said phase variable to vary across detector elements of said detector.

According to one embodiment, said detector element is a single detector pixel or group of pixels such as a detector module. In other words, the fluctuation is modelled to depend on pixel position so can vary from pixel to pixel (but not necessarily over all pixels) across the detector. Alternatively, there is only pixel-group dependency. In other words, the phase variable depends on pixel-group position rather than on individual pixel positions. One pixel group may be for instance a respective one of the detector modules. In one embodiment, the offset within each or some or all detector modules is constant but may differ from detector group to detector group.

According to one embodiment, the phase variable includes instead or in addition to a spatial dependency, a temporal dependency to model a change over time of said fluctuation.

The fitting of the additional reference phase variable as proposed in one embodiment amounts to a robust concept for data acquisition and image reconstruction in grating-based phase contrast imaging. Robustness is achieved by mathematically modelling the drift of fringes during the acquisition and by fitting the model parameters during reconstruction concurrently with the imaging variables. Better robustness helps reducing image artifacts.

In particular an increase in robustness has been observed by Applicant with the proposed method. In particular, the proposed method is less sensitive to drift or vibration-induced variations of the fringe phase which cause a change in the reference phase. It is precisely these fluctuations that are caused by mechanical (even or thermal) influence that the proposed system can account for. The requirement for a high reproducibility of the fringe pattern between the air scan (calibration measurements) and the object scan can be lowered. As a consequence of the proposed method, fewer air scans may be required because the proposed system has been observed to account for or even correct (during iterative reconstruction) wrong or inaccurate calibration data.

According to a further aspect there is provided an imaging arrangement comprising:

a signal processing system of any one of the above mentioned embodiments; and an X-ray imager comprising an interferometer and an X-ray detector for supplying the projection data.

According to a further aspect there is provided a computer program element which, when being executed by a processing unit is adapted to perform the method.

According to a further aspect there is provided a computer readable medium having stored thereon the program element of claim.

DETAILED DESCRIPTION OF EMBODIMENTS

Figure 1:
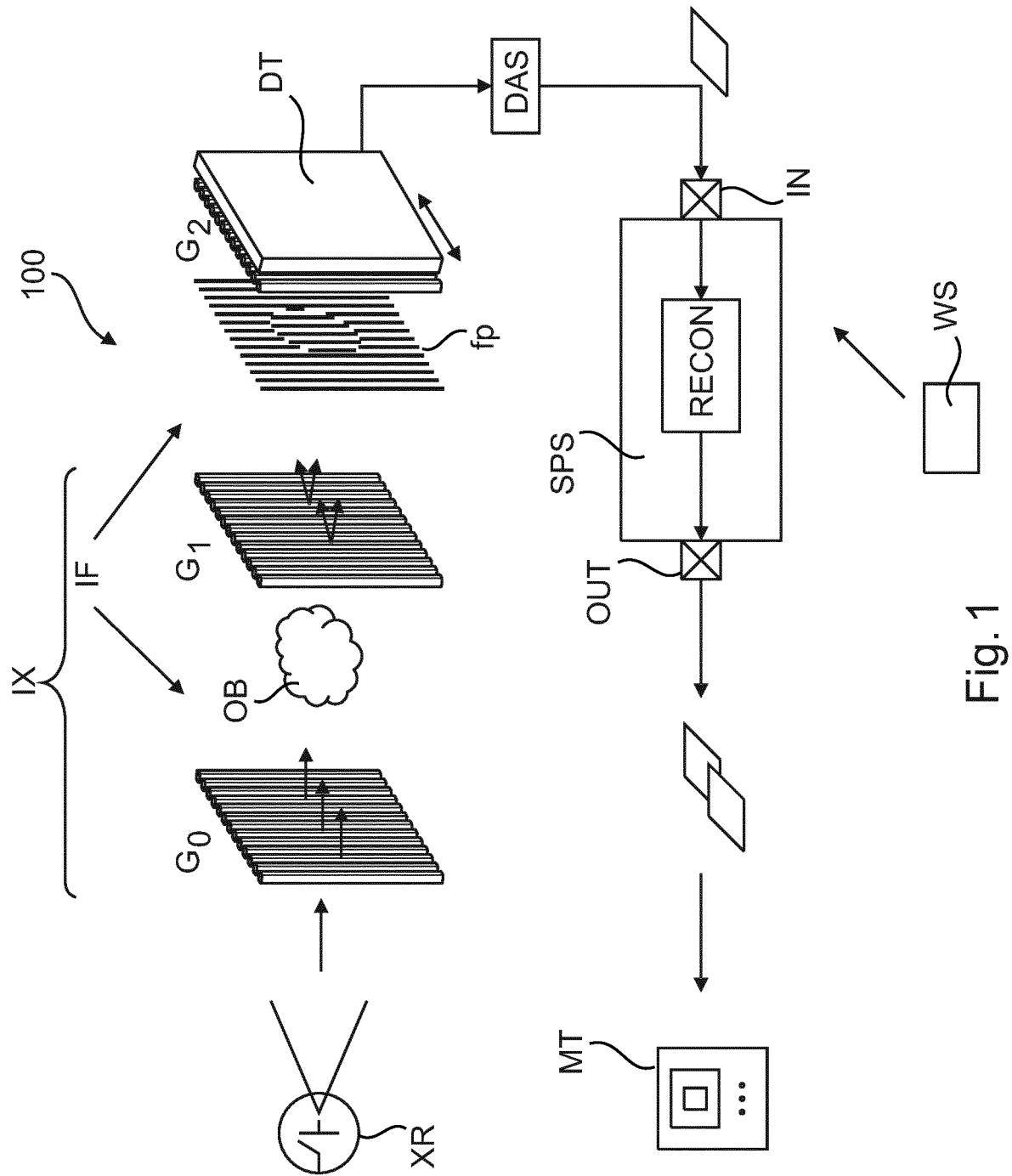
FIG. 1 shows a block diagram of an interferometric X-ray imaging arrangement.

With reference to FIG. 1, there is shown a schematic block diagram of an imaging arrangement 100. Broadly, the imaging arrangement includes an X-ray imaging apparatus ("imager") IX including an interferometric arrangement IF.

The interferometric arrangement IF includes one or two gratings arranged between the X-ray source XR and a detector DT. There is an examination region between the X-ray source and the detector and between at least two of the gratings.

The imaging or examination region is suitable to receive an object OB to be imaged. The object is animate or inanimate. An animate object includes for instance an animal or human patient or at least a part thereof (region of interest) to be imaged.

X-ray radiation emitted from a focal spot of X-ray source XR interacts with the gratings of the interferometer IF and the object and is then incident on the radiation sensitive surface of detector DT formed by a plurality of detector pixels. The incident radiation causes electrical signals which are picked up by a data acquisition system DAS and are converted into digital projection data. Because of interaction with the interferometer IF (more of which further below), this projection data is referred to herein as interferometric projection data.

The interferometric projection data is then processed in a manner to be described in more detail below by a signal processing (sub-)system SPS to produce output images which can then be stored on a data base and/or can be rendered for view on a monitor MT or can be otherwise image processed.

The signal processing system SPS may run as a software routine on a workstation WS. The workstation WS on which the signal processing system SPS is installed may be arranged to receive the projection data in a wireless or a wired network from the imager IX The projection data may be received as they are supplied by the imager or they may be received later from a memory of database. The work station may not necessarily be associated with the imager IX as the proposed signal processing sub system SPS may be run on essentially any general purpose computing device and the projection data can be supplied thereto for instance by a memory dongle via USB (universal serial bus) or by any other suitable interface.

Preferably, the imager IX is arranged as a tomographic imaging apparatus the optical axis which is shown in a horizontal arrangement running from the focal point of the X-ray source to the detector. This axis can be changed so as to acquire projection data from multiple projection directions around the object (not necessarily in a full revolution, a 180° rotation may be sufficient, or even less in tomosynthesis, etc). The object OB is thought to reside at an iso-center in the examination region whilst at least the X-ray source (in some embodiments together with the detector) and some or all of the interferometer rotates around the object in a projection data acquisition operation. In yet other embodiments, the relative rotation is achieved by rotation of the object OB.) The projection data can be processed, more specifically can be reconstructed, by the signal processing sub system SPS into cross sectional images revealing the internals of the object OB. By optionally advancing the object through the examination region, multiple cross sectional images can be obtained which can be combined together to form a 3D image volume of the object.

The imager IX is capable of producing phase contrast and/or dark field (cross section) images. In some embodiments, but not necessarily in all embodiments, there is also a third image channel for a conventional attenuation (cross section) image. The attenuation image represents spatial distribution of attenuation coefficient across the object in the respective section plane, whilst the phase contrast and the dark-field images represent spatial distribution of refractive activity of the object and small angle scattering (caused by micro structures in the object), respectively. Each of these images may have diagnostic value for a given diagnostic task at hand.

The capability of imaging for phase contrast and/or dark field signals comes about by operation of the interferometer IF. The interferometer IF comprises in one embodiment two gratings G1 (sometimes referred to a phase grating) and G2 (sometimes referred to as analyzer grating) arranged at a specific distance to each other. Preferably G2 is an absorber grating and G1 is a phase or absorber grating. In one embodiment, the two gratings are arranged downstream the examination region (in particular the objet OB), so that, during the imaging, the two gratings are situated between the object and the detector. The examination region in this arrangement is then between X-ray source and the grating pack formed by the two gratings G1 and G2.

In case the X-ray radiation is incoherent, there is a source grating G0 arranged between focal spot of XR source and the object to increase the coherence of the emitted radiation. The described interferometric set up is known as Talbot (without G0 grating) or Talbot-Lau (with G0 grating) interferometer. The distance between G0 and G1 and between G1 and G2 are specifically adjusted according to the Talbot-Lau set up that has been described elsewhere. The distances between G0 and G1 and between G1 and G2 must be finely tuned to fit the requirements of Talbot distance which in turn is a function of the "Pitch" (that is, the spatial period of the grating rulings) of the respective grating. However, if G1 is configured as an absorber grating, there is more freedom to change distances and pitches. The same holds true if G1 is a phase grating, but with a non-rectangular cross section (non-binary grating). See for instance, A Yaroshenko et al in "Non-binary phase gratings for x-ray imaging with a compact Talbot interferometer". Optics Express, Vol 22, No 1 (2014), pp 548-556.

As an alternative to the above described interferometer, inverse grating geometries are also envisaged herein where one of the two interferometer gratings (G1) is positioned between the XR source and the object OB in the examination region whereas the other (G2) is between the examination region and the detector.

Figure 2:
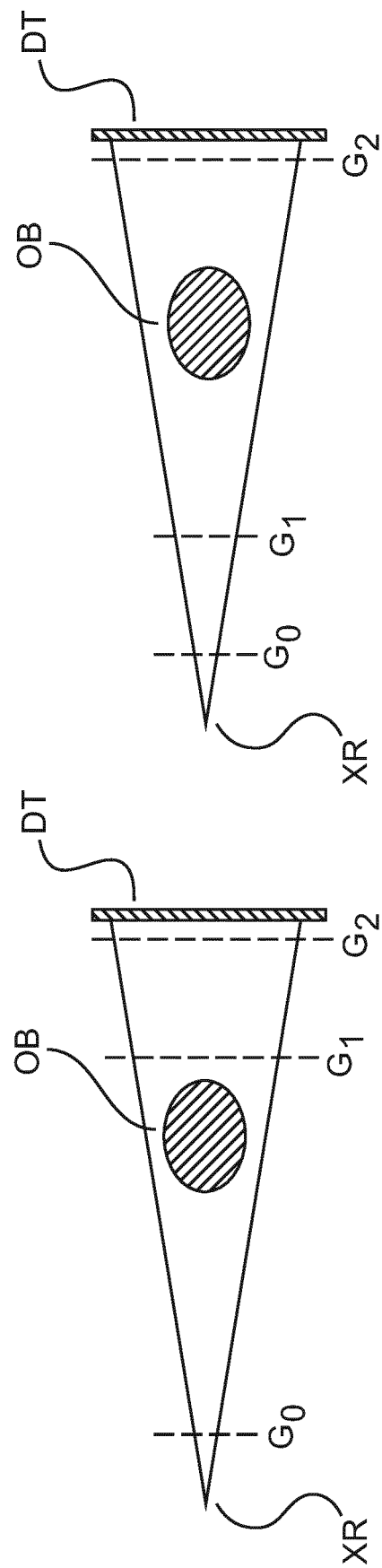
FIG. 2 shows different interferometer geometries.

FIG. 2 is a schematic illustration of these two interferometer geometries envisaged herein. The interferometer geometry on the left corresponds to the situation in FIG. 1 and is referred to herein as the direct geometry. In this geometry the object resides between the XR source (and—if present—the source grating G0) and the phase grating G1. The interferometer geometry on the right is referred to herein as the inverse geometry. In this geometry, the object OB resides between grating G1 and grating G2 or the detector if the functionality of grating G2 is integrated into the detector DT. Although both interferometer geometries are envisaged herein, the inverse geometry has some distinct advantages from a practical point of view. For instance, in the inverse geometry the grating with the finest pitch is G0 in inverse geometry (but G2 in direct geometry). Thus the grating that is most challenging to manufacture is also the smallest one which allows cost savings. Furthermore, the additional attenuation caused by G1 takes place before the patient, which is desirably as it reduces radiation dose applied to the object OB. Yet further, because of the diverging nature of the beam and because the phase grating G1 is located closer to the source XR in inverse geometry than it is in direct geometry, the size of the phase grating is smaller, a fact that further helps reducing cost.

Irrespective of the grating geometry used, assuming for a moment that there is no object OB present in the examination region the coherent radiation emerges on the far side of G0, interacts with the interferometer G1, G2 to produce an interference fringe pattern fp, in particular, fringes of a Moiré pattern, which can be detected at the detector DT. To achieve this pattern, the two gratings of the interferometer are slightly de-tuned (for instance by slightly tilting the two gratings G, G2 relative to each other). This Moiré pattern fp, which we will refer to herein the "reference fringe pattern" fp, has a certain fixed reference phase, reference visibility and intensity, all of which are encoded by the reference fringe pattern fp. The reference pattern is solely the result of the interferometer's presence (for a given radiation density). In that sense it can be said these quantities, in particular the reference phase, is a property of the interferometer as such and it is therefore apt to say that the interferometer "has" said reference phase, said reference intensity and said reference visibility.

Now, if the object to be imaged is introduced into the examination region this object will interact with the coherent radiation to which it is now exposed to, in other words, the coherent radiation will be partly absorbed, refracted and scattered. The result of this object interaction is yet another interference pattern, different from the reference pattern, which will be observed at detector DT. The interference pattern induced by the presence of object OB can be understood as a perturbed version of the reference fringe pattern when there was no object present in the examination region. The reference data of the reference fringe pattern fp are usually acquired in calibration measurement also referred to as an "air scan". The actual object measurements are then acquired in a second scan when the object to be imaged is present in the examination region. One way to sample the reference pattern is by inducing, during X-ray exposure and for any given position of the optical axis of the scanner IX, a sample motion between the interferometer and the object and/or the X-ray radiation. In this manner, the interferometric projection data it acquired and can then be processed as will be explained in more detail below to extract the sought after images of attenuation, phase contrast and/or dark field. More particularly, this relative sample motion can be introduced for instance by focal spot sweeping or the "phase stepping" technique in which one of the gratings G1 or G2 or G0 is moved relative to the other. In alternative embodiments, the interference pattern can be sampled by sampling across neighboring pixels so no sample motion is required in these embodiments. The upshot of any of these sampling or interference pattern data collections is, that for each projection direction i, a series of measurements is acquired per detector pixel j.

The interferometric projection data is reconstructed into cross-sectional images of the object by using a preferably iterative reconstruction algorithm. The iterative reconstruction algorithm fits three image variables, one for each of the three data channels (phase contrast, attenuation, and dark field imaging) to the measured projection data to arrive at the cross sectional images for each of the channels. Conceptually, the iterative reconstruction algorithm uses a forward signal model that explains the measured interferometric data (which are essentially intensities) as combined contributions from three different physical effects: attenuation, refraction, and small angle scattering.

As such, reconstruction algorithms of the iterative type have been previously described for instance by A. Ritter et a in "Simultaneous maximum-likelihood reconstruction for X-ray grating based phase-contrast tomography avoiding intermediate phase retrieval", available online, visit arXiv: 1307.7912 [physics.med-ph], version as per 30 Jul. 2013. However, it will be understood by those schooled in the art that Ritter et al merely provide an example for a possible reconstruction setting within which the proposed system and method can be practiced and other settings are excluded herein.

In Ritter et al and in similar iterative type reconstruction approaches, the reconstruction problem is formulated as an optimization problem in terms of a cost or objective function. The cost and objective function is made up from data term that represents the actually measured interferometric projection data (that is, intensities) and this is compared against forward projections as per a forward signal model. Additionally, in some embodiments (but not necessarily all embodiments), a penalization term or regularizer term is used to enforce certain smoothness properties in space or time, or to incorporate other a-priori information about the unknown images to be reconstructed.

Conceptually, the examination region where the imaged object resides (during acquisition of the projection data) can be thought of as divided into a 3D grid of 3D locations. This grid defines the imaging domain. Image elements ("voxels" or "blobs") of the image(s) to be reconstructed are defined as image values assigned to these locations in the imaging domain. The reconstruction operation aims at finding an "optimal" assignment of image values that best "explains" the actually measured projection data.

Briefly and referring back to FIG. 1, a signal processing system is proposed herein and his includes an input port IN for receiving the interferometric projection data converted from signals detected at detector DT. This data is then fed into a reconstructor RECON which runs an iterative reconstruction scheme based on the objective function to produce in one or more iterations the sought after images by fitting variables for these images to the signal model. The reconstructed imagery is then output at output port OUT and can then be stored or viewed or otherwise processed as required.

The fitting operation in the iterative reconstruction entails performing one or more forward projections based on the forward signal model. The forward projections are performed on the voxels through the imaging domain and onto a plane (projection domain) located at the detector DT. The forward projections are performed along geometrical rays that are cast from the XR source towards a detector pixel position in said projection domain plane through the image volume. During iterations, image values at the voxel locations are generated and these are forward projected to check consistency with the measure projection data. To achieve better accuracy, the forward projections are scaled herein to account for certain magnification effects that have been observed to occur in relation to the phase contrast signal.

Figure 3:
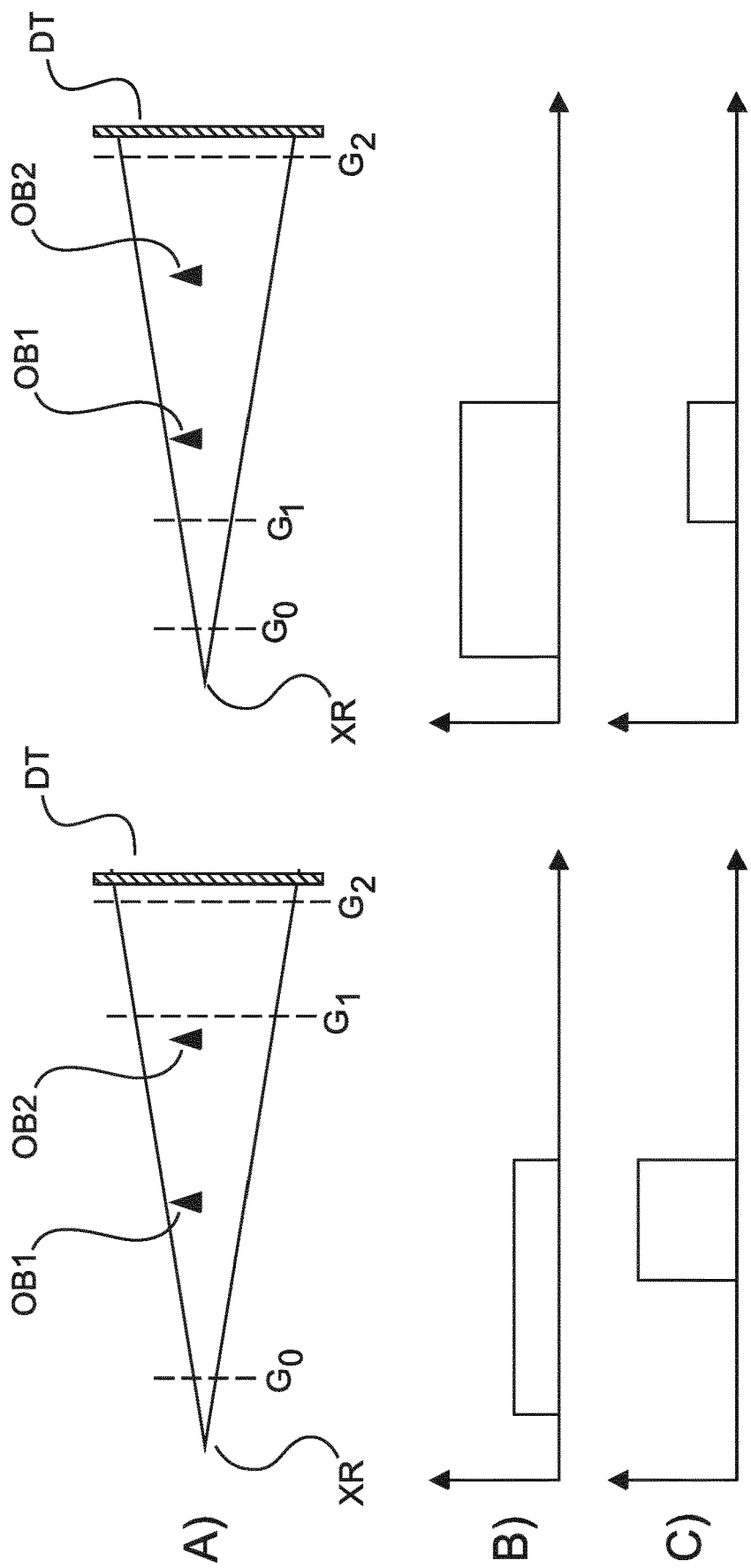
FIG. 3 shows magnification effects in relation to the two interferometer geometries.

More specifically, phase contrast signal sensitivity of the two geometries appears to be dependent on the position of the object along the beam path. The phase contrast sensitivity is illustrated in FIG. 3 for the direct (left column) and inverse interferometer geometry (right column). It can be seen, that a signal strength of a wedge-shaped object scales with the magnification from G0 to G1 in direct geometry, but with magnification from G2 to G1 in inverse geometry. Specifically, row A) illustrates two sample objects OB1, OB2 (shown as two wedges) in two interferometric geometries. Rows B,C) illustrates differential phase signal strength as a function of detector pixel position (measured from the optical axis of the imager IS) for objects OB1, OB2, respectively. It is proposed herein a signal processing system SPS that implements a (preferably) iterative reconstruction whose forward projection operation accounts for this sensitivity change along the beam path in particular for the phase contrast signal and, optionally, also for the dark-field signal. Specifically, it is proposed to more correctly model the illustrated magnification effect in particular for the phase contrast signal by suitable scaling into the forward projection of the iterative reconstruction. Yet more specifically, for direct interferometer geometries, the forward projection accounts for the observed fact that the phase contrast or dark-field signal strength scales with magnification of the object OB from G0 to G1. Alternatively, for inverse geometry interferometers, the forward projection accounts for the "dual" fact that the phase contrast or dark-field signal strength scales with magnification of the object OB from G2 to G1.

In another embodiment, phase stepping is performed in order to allow for a pre-processing step in SPS, namely the phase retrieval being "decoupled" projections of the attenuation, and the small-angle scattering and a differential projection of the refractive index. Subsequently, system SPS performs a preferably iterative reconstruction of the refractive index with the magnification as described above.

In one embodiment, the reconstructor RECON is further configured to account for fluctuations of reference phase of the interferometer IF.

Figure 4:
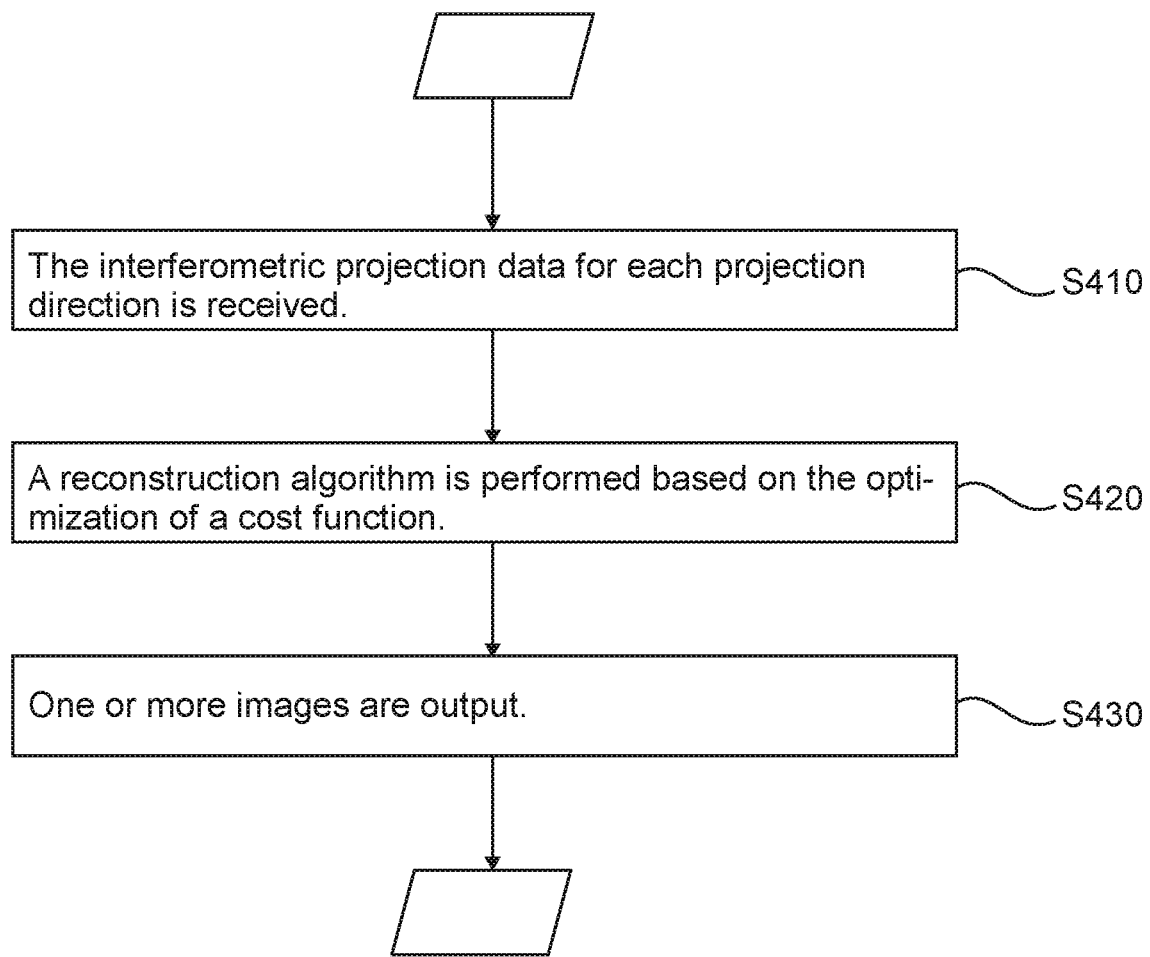
FIG. 4 shows a flow chart of a signal processing method.

Operation of the proposed re-constructor RECON is now explained in more detail with reference to the flow chart in FIG. 4 with the understanding the method steps described below constitute a teaching in their own right and as such are not necessarily tied to the system architecture of FIG. 1.

At step S410 the interferometric projection data for each projection direction is received.

At step S420, a reconstruction algorithm is then performed based on the optimization of a cost function. More particularly, the reconstruction is formulated as a minimization problem based directly on measured intensities. Yet more specifically, the reconstruction of the linear attenuation coefficient $\mu$ (attenuation image), the electron density $\delta$ image (which corresponds, up to a proportionality factor, to the phase contrast image), and the scatter coefficient $\varepsilon$ (dark-field image) is obtained by minimizing the cost function $\Delta^2$ to so fit the image variables $\mu$, $\delta$, $\varepsilon$ to the interferometric projection data J:

$$\Delta^2(\mu, \delta, \varepsilon) = \sum_{i,j} \frac{1}{\sigma_{ij}^2}(J_{ij} - I_{ij}(\mu, \delta, \varepsilon))^2 \quad (1a)$$

In the expression (1a), i indexes all projection angles (or more generally i is a readout index) and j all pixels of the detector.

It is of note that the formulation of the cost function as per (1a) has the structure of a least squares problem which is a consequence of assuming an underlying Gaussian noise for the measurement. However this may not be so necessarily and other, more general structures of (1a) in the form of:

$$\Delta(\mu, \delta, \varepsilon, \psi) = \sum_{i,j} [\Lambda(J_{ij}, I_{ij}(\mu, \delta, \varepsilon))] \quad (1b)$$

are also envisaged herein where $\Lambda$ is a function that represents the statistical assumptions that are thought to govern the measurement process. In particular, statistical models other than Gaussian. e.g. Poisson, are also envisaged herein.

In optimization problems (1a)(1b), J denotes measured intensities with statistical variance $\sigma$ and I denote the forward calculated intensities according to the following forward signal model for the measured densities:

$$I_{ij}(\mu,\delta,\varepsilon) = I_{ij}^{(0)} \exp(-\int_{L_{ij}} \mu dl)(1 + V_{ij}^{(0)} \exp(-\int_{L_{ij}} m(l)\varepsilon dl)\sin(\phi_{ij}^{(0)} + \partial_x \int_{L_{ij}} m(l)\delta dl)) \quad (2)$$

where $I_{ij}^{(0)}$, $V_{ij}^{(0)}$, and $\phi_{ij}^{(0)}$ denote the reference data obtained in the "blank" or air scan as: intensity, blank visibility, and reference phase (that is, phase of the Moiré reference fringe pattern fp) for the pixel j at readout i, respectively, $L_{ij}$ denotes the line connecting the source at projection angle/readout i and the detector pixel j at readout i, and $\mu$, $\delta$, $\varepsilon$ denoting the imaging variables to be fitted to the measured interferometric intensity projection data J. "l" denotes the voxel locations over which one integrates along line $L_{ij}$ to compute the line integral expressions in (2). The term "readout i" as used herein indicates measurements collected at different projection angles but also measurements collected at different times for the same projection direction. The partial derivation $\partial_x$ is taken in the direction perpendicular to the grating orientation that is perpendicular to the normal to the grating plane.

In forward model (2), the function m(l) represents the newly proposed scaling factor to correctly account for magnification effect cause by distance l of a voxel location l from the interferometer IF.

Figure 5:
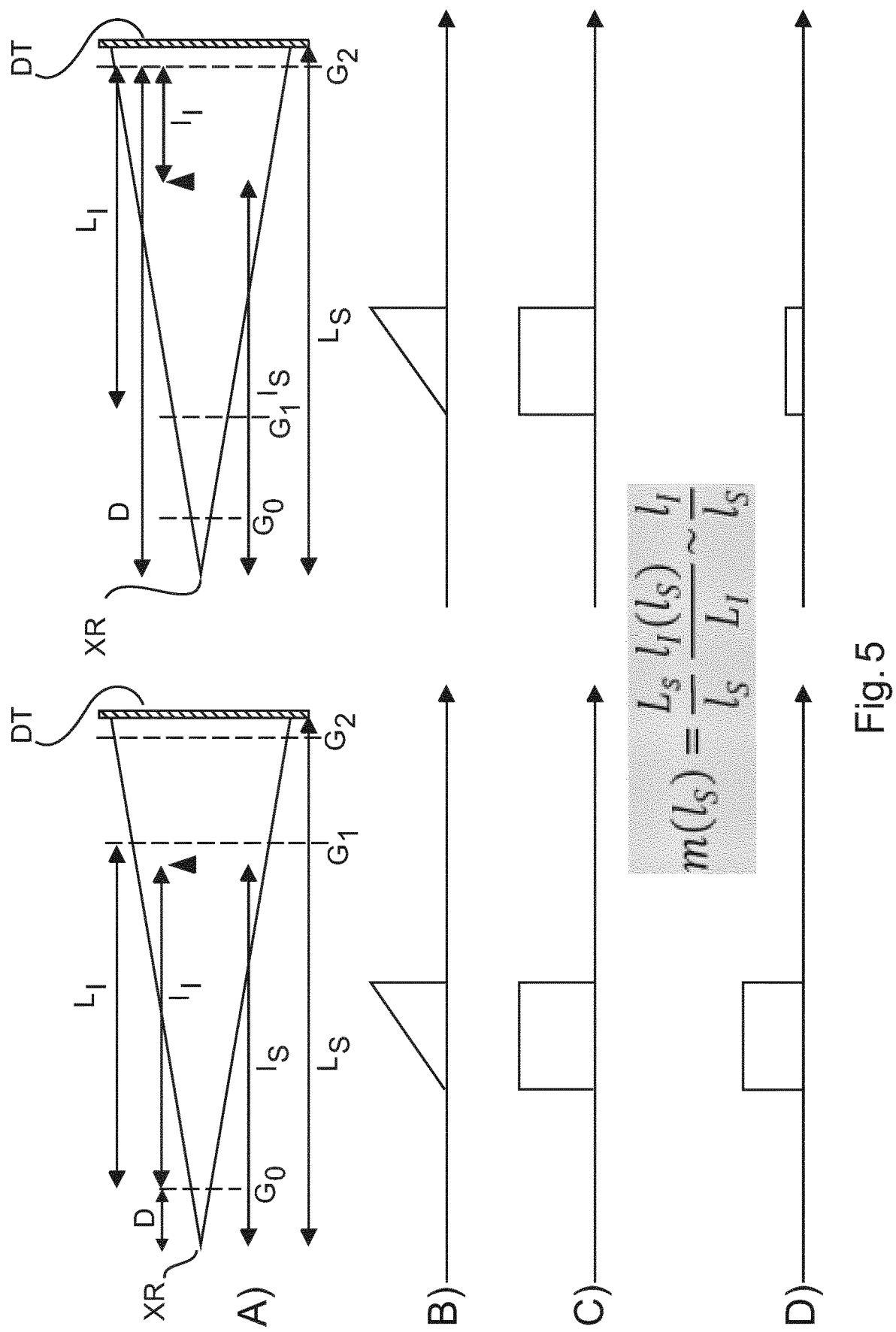
FIG. 5 is an illustration of a forward projection operation for image reconstruction.

The scaling factor m is illustrated in more detail in FIG. 5. The scaling factor m is shown for the two interferometer geometries (row A).

In the direct geometry (left in FIG. 5), the following notation is used for the distances involved (these distances are measured by casting a geometrical ray from the focal spot of source XR to a certain pixel position of the detector DT):

$L_I$=distance between G0 and G1
$l_I(l_S) = l_S - D$=distance between voxel location and G0 (with D being the distance from source XR to G0)
$l_S$=distance between voxel location and source XR
$L_S$=distance between detector DT and source XR For the inverse geometry (right), we have:
$L_I$=distance between G1 and G2
$l_I(l_S) = D - l_S$=distance between voxel location and G2 (with D being the distance from source XR to G2)
$l_S$=distance between voxel location and source XR
Ls=distance between detector DT and source XR In both geometries, the scaling factor is $m(l_S) = L_S/l_S * l_I(l_S)/L_I$. The scaling factor is proportional to $l_S/l_I$ because $L_S$ and $L_I$ are constants. The distances involved in computing the scaling parameter $m(l_S)$ can be seen to fall into two broad categories: distances in relation to the interferometer (interferometer distances) and distances in relation to the source (source distances). In other words, the scaling factor is obtained by scaling a source distance ratio with an interferometer distance ratio. In particular, the interferometer distances include inter-grating distances, that is, distances LI between gratings. Furthermore, the formula m(ls) for the scaling factor can be seen to be invariant under interferometer IF geometry (inverse or direct) but the distances used to compute the scaling factor, in particular the inter-grating distances and the distances between voxel location and interferometer are different for each of the two geometries.

All distances involved are either design parameters of the imaging system IS or, in case they relate to voxel location, can be readily computed from the known imaging geometry. For calibration purposes, the signal processing system SPS may include a calibration interface (no shown) where the user can supply updated distances in case these are found to have changed due to change of equipment, wear, environmental changes, etc.

Use of the scaling factors in forward projection during iterative reconstruction for direct and inverse geometry is illustrated in FIG. 5. Although the illustration is for a single object only (as shown a small dark wedge), this is not limiting because the (conventional) forward projection is a simple sum of the contribution of all objects in the field of view. Since the subsequent differentiation is a linear operator, it is possible to exchange the differentiation and the re-scaling operation.

In one embodiment, the forward projection reads in a ray driven manner: that is, for each detector pixel, a geometrical ray $L_{ij}$ is cast from the source to this pixel. Then, for each voxel location along the ray, the current voxel values (as computed in the current iteration cycle) are sampled in the image domain. The sampled value is then scaled with the appropriate magnification m(ls) as shown in FIG. 5.

The sampled and scaled values along the line $L_{ij}$ are then added ("accumulated") and the so accumulated scaled values are then stored as a respective forward projection value for this ray. The first derivative (taken in a direction across the trenches of the gratings) is then computed (row C) from the so scaled and accumulated projection values to complete the forward projection for the phase contrast channel (row D). The slope of the differentiated forward projection is proportional to $l_s/L_s$. Scaling with $L_s/l_s$ ensures that the slope is independent from voxel location $1_r$.

As an illustration, row B) shows non-differentiated, conventional projection data. The width of the projection can is proportional to $L_s/l_s$ whilst the height is independent of the voxel location $l_r$.

Differentiation is required in ray driven approaches because the phase channel contribution is differential in nature as can be seen the right most term in the forward model (2). Said differently, the phase contrast does not directly contribute to the detected intensities directly but it is only the differential of the phase contrast signal that contributes to the detected intensities. It should be noted, that du to linearity, the scaling operation may be applied instead after the differentiation.

The proposed scaling can be used for any ray-driven forward projection, for instance if Joseph's method is used for image value sampling along the respective rays. See for instance P Joseph in "An Improved Algorithm for Reprojecting Rays through Pixel Images" in IEEE Transactions on Medical Imaging, Vol 1, Issue 3, pp 192-196 (1982). Other examples for ray driven projection techniques (all envisaged herein) are discussed by Rolf-Dieter Bippus et al in "Projector and Backprojector for Iterative CT Reconstruction with Blobs using CUDA", 11th Fully 3D conference, Potsdam, 11-15 Jul. 2011, conference proceedings, pp 68-71, available at fully3d.org/2011/Fully3D2011Proceedings.pdf.

Figure 6:
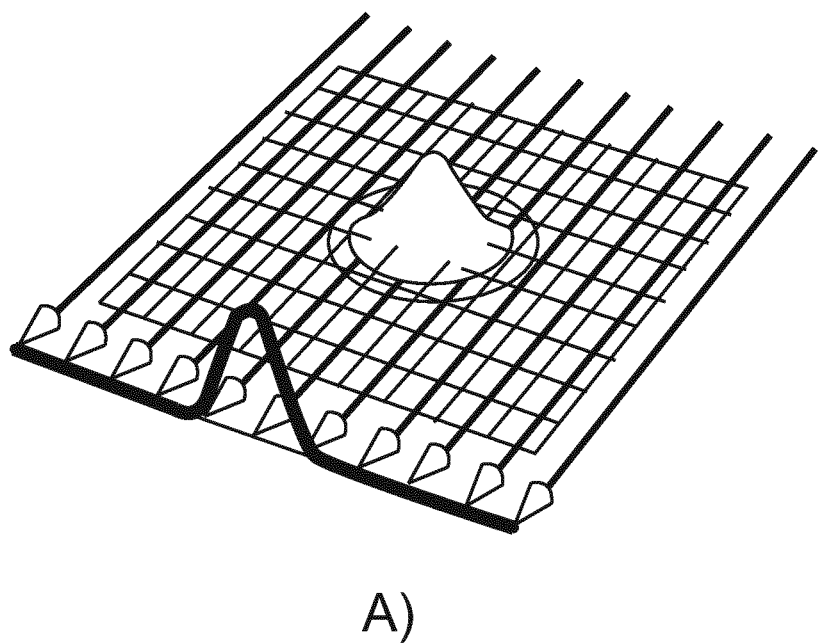
FIG. 6 shows types of basis functions for image reconstruction.
Figure 6:
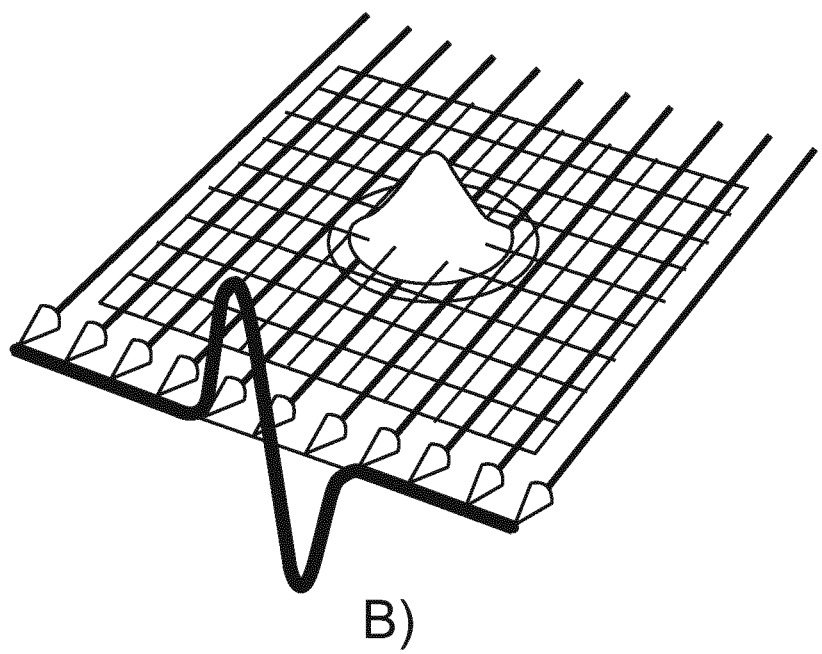
Figure 7:
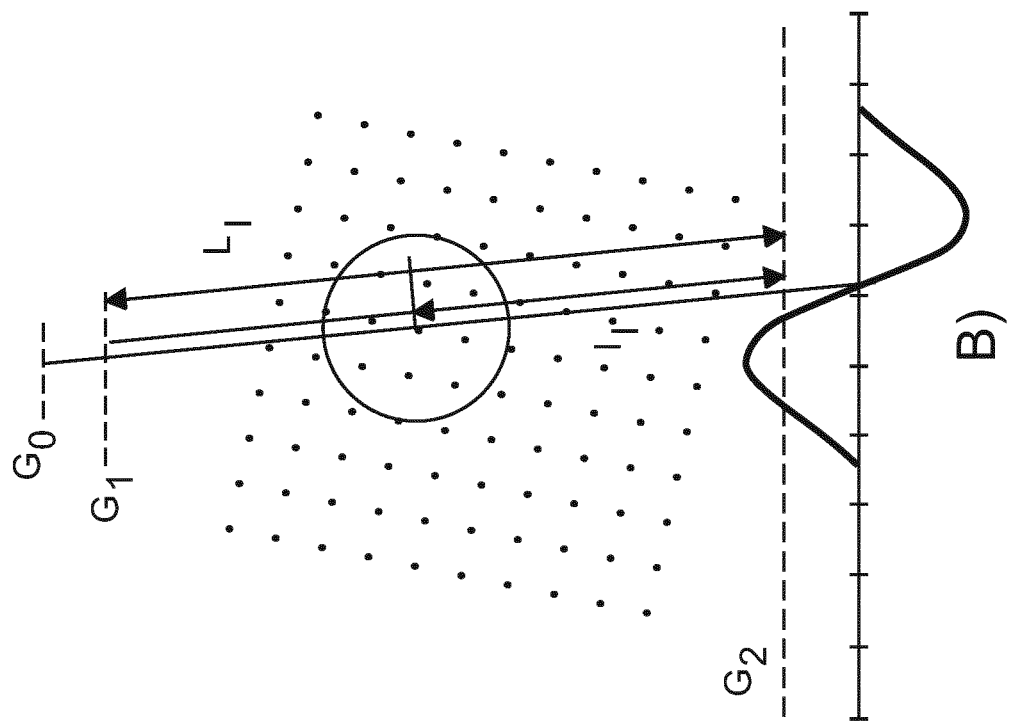
FIG. 7 is an illustration of a forward projection operation using types of basis functions as per FIG. 6.
Figure 7:
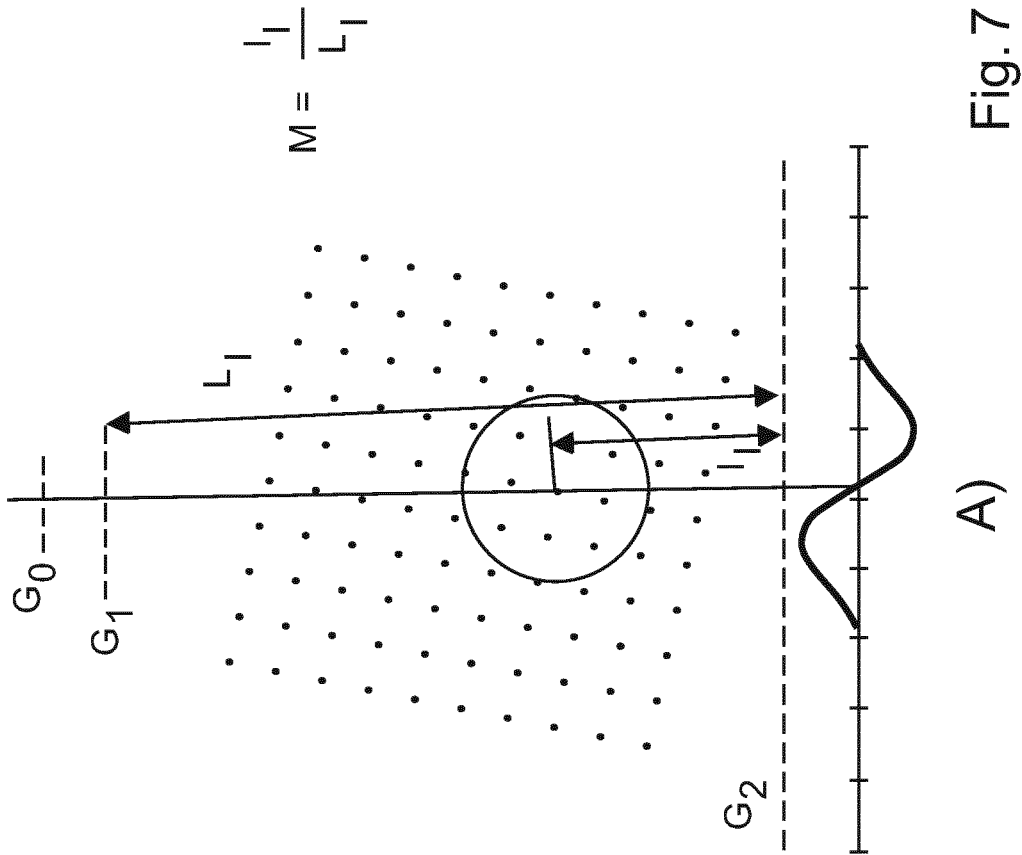

In an alternative embodiment, a basis-function driven forward projection scheme is used. An exemplary embodiment for this is the case where spherical basis function, such as Kaiser-Bessel functions ("blobs") are used. Other types of spherical or non-spherical basis functions are envisaged in alternative embodiments. The use of blobs and their forward projection is illustrated in FIGS. 6,7. The general concept is that the entire image domain is represented by a linear combination of some basis functions defined at each voxel location in the image domain grid. As the forward projection is linear, the forward projection can be explained by explaining the forward projection of a single basis function. This is illustrated in FIG. 6, where A) illustrates the projection of a basis function for the attenuation channel and B) for the phase contrast channel.

The basis function based forward projection can be implemented by pre-computing the projections for different projection directions of the basis function and by storing the pre-computed projections in a lookup table (LUT). The computational effort for forward projection computation may thus be reduced by merely calculating the projection of onto to the detector DT of the center of a symmetric basis function and to look up from the LUT the complete contribution of the basis function to the projection. A related concept for blob-type basis function concept has been described in Koehler et al in "Iterative reconstruction for differential phase contrast imaging using spherically symmetric basis functions", Med. Phys, 38(8), 4542, 2011. The basis function approach with direct differential formulation may be used instead of or in combination with the ray driven schemes mentioned above.

FIG. 7 illustrates how the sensitivity change for the phase contrast signal along the projection direction is reflected in the forward projection footprint of as basis function. Specifically, using differential basis functions (eg, blobs) then there is no inherent scaling with the magnification from source to detector. Therefore, only the magnification from G2 to G1 needs to be taken into account for inverse geometry (and the magnification from G0 to G1 in direct geometry). As mentioned, the basis function projections may be pre-computed and stored in the lookup LUT.

The scaled forward projection as described above is repeated throughout the course of the iterations to enforce consistency of the solution with the measured interferometric projection data J. At the conclusion of the iterations, in particular the phase contrast image δ is output at step S430. At step S430, a single one, a selection of two, or all of the reconstructed images μ, δ, ε are output. Output can occur during the iteration at some or each step or at the conclusion of the iterations. Outputting may include in one embodiment converting the phase contrast image into an electron density image or vice versa.

In one embodiment, an extension of the above forward signal model (2) is envisaged as per:

$$I_{ij}(\mu,\delta,\varepsilon)=I_{ij}^{(0)}\exp(-\int_{L_{ij}}\mu dl)(1+V_{ij}^{(0)}\exp(-\int_{L_{ij}}m(l)\varepsilon dl)\sin(\phi_{ij}^{(0)}+\psi_i\partial_s\int_{L_{ij}}m(l)d\ dl)) \quad (3)$$

This extended model (3) now includes, in addition to the three imaging variables, a further, dedicated fitting variable ψ to account for a fluctuation of the reference phase of the interferometer IF, or, said differently, for the reference interference pattern caused by the interferometer in the absence of the object OB in the X-ray beam. This is because Applicant has observed that phase contrast and dark field imaging, especially in computed tomography context, may suffer from severe artifacts which are caused by such fluctuations or changes, also known as drifts, of the reference interference pattern, his is especially true in CT where during the rotation buckling and other mechanical changes occur that induce those fluctuations. Also thermal expansion or contraction has been identified to cause these fluctuations. It is therefore proposed herein to not only include fitting variables for the three image channels into a common reconstruction problem but also to include, in addition, a dedicated fitting variable that accounts for the fluctuations of the reference phase to reduce those artifacts mentioned. Indeed, these artifacts in the reconstructed imagery can be thought to arise if the effect caused by the reference phase fluctuation is incorrectly attributed to the other three fitting variables for the three channels. The adoption as proposed herein remedies or at least reduces artifacts because the judicious placement (on which more below) of this dedicated variable for the fluctuations of the reference phase prevents incorrect attribution of this effect to the other variables (absorption, refraction or small angle scattering). Said differently, Applicant proposes to increase the "pool" of fitting variables by introducing said fluctuation variable in a direct reconstruction algorithm to arrive in particular at artifact reduced phase contrast and/or dark-field cross section images.

In view of the extended forward model (3), the optimization problem is now reformulated as:

$$\Delta(\mu, \delta, \varepsilon, \psi) = \sum_{i,j} [\Lambda(J_{i,j}, I_{ij}(\mu, \delta, \varepsilon, \psi)] \quad (1c)$$

Applicant observed that reconstruction based on the above minimization problem (1c) helps avoid or reduce the angular blurring generated by the dedicated phase-retrieval based reconstruction in the sliding window technique for instance. Also. Applicant has found that not only does the blank scan interferometer phase (phase of the fringe pattern) $\phi_{ij}^{(0)}$ drift or fluctuate during acquisition, but also that this phase reference fluctuation is a critical (if not the most critical) parameter in terms of artifact expression. Reference phase fluctuation of the interferometer IF is addressed herein by establishing an empirical forward model as per (3) including the dedicated fitting variable ψ for possible modes of fluctuations of the blank scan phase due to drift. As can be seen, the formulation of eq (1c) is an extension of eq (1b) above. A similar extension by variable ψ of formulation (1a) is also envisaged.

In one embodiment, a constant phase offset ψ for all detector pixels and readouts j is assumed as per (3). That is, the same value is used for all pixels and all readouts j. However spatial or temporal modelling refinements are also envisaged herein.

For instance, the offset modelling may be refined in some embodiments by still assuming the same offset for all detector pixels but now with a dependency on the readout i. Notationally this can be indicated by using $\psi_i$ instead of ψ in (3). In particular, this dependency allows modeling changes of the offset from projection angle to projection angle. This can be further expanded yet by modeling the fluctuations over both dimensions of the readout i, that is, over projection direction and the time at which the collection occurs.

Of course this comes at a computational cost because the number of variables to be fitted is now increased compared to the case with constant offset.

The 1 unknown fluctuation offsets are incorporated as variables into the cost function. More specifically, as can be seen above at (3) the architecture of the forward signal model includes a first exponential factor which accounts for the attenuation. The expression in brackets (1+ ... ) includes a term that accounts for the change in visibility. In addition there is a further, sinusoidal term factor that accounts for the contribution from refraction. The reference phase fluctuations are modeled as an additive term W in the argument of said sinusoidal term. The one or more phase fluctuation variables y are added to the experimental blank scan reference phase $\phi_{ij}^{(0)}$ to model the phase change as an additive perturbation of the blank scan $\phi_{ij}^{(0)}$. The additional term allows modeling changes caused by imperfections of the interferometer caused by mechanical deformations in response to thermal changes or simply by effect from gravity during the rotation of the interferometer during the CT scan. These mechanical effects will likely change the mutual orientation of the two gratings and hence will perturb the "detuning" earlier mentioned to establish a suitable Moiré pattern (having a period of sufficient length).

It will be understood that any mathematical equivalent of the above eqs (2.3) is envisaged herein which includes in particular numerical approximations thereof. For instance, it will be understood by those skilled in the art that the sinusoidal expression may be replaced in approximation by a suitable polynomial expression (Taylor series expansion), etc.

While a constant phase offsets or one that varies with readout i as discussed above seems to be a sufficiently accurate model for accounting to drift in some setups, it might be too simple for larger systems with a gantry rotating at high rpms. It is therefore proposed herein, as a further spatial modeling refinement and in an alternative embodiment, to model the reference phase offset with a dependency on j, that is, there is now a dependency across pixel positions. Notationally, this modelling approach is indicated by using $\psi_j$ instead of ψ in (3). This fluctuation modelling can be implemented, in a polynomial (of order n≥1) fashion, across the detector pixels j. Models other than polynomial are also possible.

If the detector is built from different modules, a slight coarsening of the pixel-to-pixel variation for the offset modelling is to vary the offset merely as a function of detector module position. The detector module offset dependency may be implemented by choosing a polynomial variation across the detector modules. Again, models other than polynomial are also possible.

In the following a further variant of the above forward model (3) will be described. As a combination of the above spatial and/or temporal dependencies for the offset, the following refinement of (3) is also envisaged allowing now a free drift parameter for each pixel j and each readout i:

$$I_{ij}(\mu,\delta,\varepsilon,\psi_{ij})=I_{ij}^{(0)}\exp(-\int_{L_{ij}}\mu dl)(1+V_{ij}^{(0)}\exp(-\int_{L_{ij}}m(l)\varepsilon dl))\sin(\phi_{ij}^{(0)}+\psi_{ij}+\partial_x\int_{L_{ij}}m(l)\delta dl)) \quad (4)$$

However, these many degrees of freedom as per (4) may call for some form of regularization. It is therefore envisaged in one embodiment to add to the cost function the following regularization term:

$$R_s(\psi) = \sum_{i,j}\sum_{k\in N_j} p_s(\psi_{ij} - \psi_{ik}) \quad (5)$$

to enforce spatial smoothness where $p_s$ is a potential function operating on the differences between the fluctuations parameter ψ, wherein $N_j$ denotes a set of indices related to pixels in the spatial neighborhood of the pixel with index j. In one exemplary embodiment, $p_s$ is the square or the absolute value of the argument. The neighborhoods $N_j$ may represent the tiling of the detector surface into the different detector modules. Also, $p_s$ may itself vary with the neighborhoods $N_j$.

Instead of or in addition to regularizing the spatial dependencies of the offset as per (5), a temporal regularizing in order to account for phase drift in time is envisaged herein in some embodiments to enforce temporal smoothness of the phase drift modelling. Temporal variation can be achieved for instance by applying an explicit, e.g. polynomial, model of the phase drift with time, or it might be desired to add a smoothness constraint on the reconstructed phase drift. For instance, in one embodiment, a temporal regularizer term having the structure $$R_t(\psi) = \sum_i\sum_j p_t(\psi_{ij} - \psi_{i+1,j}) \quad (6)$$

is introduced. Again $p_t$ is a potential function and here differences between temporally neighboring phase drifts a per the readout index i are penalized.

Referring back to spatial smoothness, this can be also achieved if a parametric model for the spatial variation of the phases due to drift is established. For instance the phase shift due to drift might be modelled for each projection i by a polynomial with unknown coefficients. In this case, the phases $\psi_{ij}$ are fitted "indirectly" by fitting coefficients $a_{i0}, a_{i1}, a_{i2}, \ldots$ for each readout i. Again, a temporal smoothness constraint can be imposed by adding a penalty on the coefficients of the form $$R_{t'}(a) = \sum_{i,c} p_a(a_{ic} - a_{i+1c}) \qquad (7)$$

where the index c runs over all coefficients.

Although in the above forward models eq (2,3), the scaling factor m(l) has been applied to both, dark-field and phase contrast channel and this is clearly preferred, alternative embodiments are also envisaged where the scaling is applied only for the phase-contrast channel.

A further advantage of the processing concept described herein is that the method can easily handle distortions of the fringe pattern and that it automatically accounts for inaccuracies in the phase stepping (e.g., inaccuracies in the step increment).

The optimization problems (1a-c) above can be solved by any suitable numerical technique such as maximum likelihood approaches, conjugal gradients, Newton-Raphson etc.

It should be noted that "optimization" as used herein may not necessarily mean that the optimization results in a global optimum but may return local optima instead. Also, depending on the CPU time and other considerations it may be opportune to abort iterations before the local or global maximum is reached, for instance if differences between successive iteration results drop below a given abortion threshold.

Although in the above embodiments a dedicated second grating (G2) was used as an analyzer grating to form the interferometer, this may not necessarily be so in all embodiments. For instance, the (analyzer) grating G2 functionality can also be integrated into the detector DT itself. What is more, the grating function can be entirely taken over by the detector itself by a judicial arrangement of the pixel geometry, in particular the inter-spacing between the pixels accordingly.

As mentioned above the proposed signal processing system may run as a software routine on a workstation. In other embodiments, the proposed SPS system may be implemented as hardware in a dedicated chip, for instance, by suitably programing as an FPGA. Hardwired chip implementations are also envisaged. The chip may be integrated in video or graphics hardware of the work station or may be integrated as a processing stage in the DAS, etc.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present disclosure. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the present disclosure.

This exemplary embodiment of the present disclosure covers both, a computer program that right from the beginning uses one embodiment of the present disclosure and a computer program that by means of an up-date turns an existing program into a program that uses one embodiment of the present disclosure.

Further on, the computer program element might be able to provide all necessary steps to fulfill the procedure of an exemplary embodiment of the method as described above.

According to a further exemplary embodiment of the present disclosure, a computer readable medium, in particular a non-transitory storage medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present disclosure, a medium for making a computer program element available for downloading is provided, which computer program element is arranged to perform a method according to one of the previously described embodiments of the present disclosure.

It has to be noted that embodiments of the present disclosure are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the present disclosure has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A signal processing system, comprising:
a memory that stores a plurality of instructions; and
processor circuitry that couples to the memory and is configured to execute the instructions to:
receive interferometric projection data derived from signals acquired by an X-ray detector of an interferometric X-ray imaging apparatus, said signals caused by X-ray radiation after interaction of said X-ray radiation with an interferometer and with an object to be imaged, said interferometer having an inter-grating distance;

perform, based on the projection data and a forward signal model of a phase contrast signal, a reconstruction operation for one or more images in an image domain of a spatial distribution of at least one physical property of said object including a refractive index, wherein the reconstruction operation is an operation in a phase contrast signal channel with the refractive index as an observable, wherein the processor circuitry is configured to perform in the reconstruction operation a scaling operation based on the inter-grating distance of the interferometer and/or on a distance of a location in said image domain from said interferometer; and output said one or more images.

2. The signal processing system of claim 1, wherein the interferometer includes a source grating and said inter-grating distance corresponds to a distance between said source grating and a further grating of the interferometer.

3. The signal processing system of claim 1, wherein the scaling operation is further based on a distance between a source grating and the detector.

4. The signal processing system of claim 1, wherein said interferometer inter-grating distance corresponds to a distance between two gratings of the interferometer.

5. The signal processing system of claim 1, wherein said distance between the image domain location and the interferometer corresponds to the distance between said image domain location and a source grating.

6. The signal processing system of claim 1, wherein said distance between the image domain location and the interferometer corresponds to the distance between said image domain location and a grating of the interferometer.

7. The signal processing system of claim 1, wherein the projection data has been acquired from different projection directions.

8. The signal processing system of claim 1, the processor circuitry is configured to fit said interferometric projection data to the signal model by adapting a plurality of fitting variables, said fitting variables including i) the one or more imaging variables for the one or more images and ii), in addition to said one or more imaging variables, a dedicated phase variable for a fluctuation of a reference phase.

9. The system as per claim 1, wherein said physical property includes any one or more of the following: i) attenuation, or ii) small angle scattering.

10. An imaging arrangement comprising:
a signal processing system of claim 1; and
an X-ray imager comprising an interferometer and an X-ray detector for supplying projection data.

11. A signal processing method, comprising:
receiving interferometric projection data derived from signals acquired by an X-ray detector of an interferometric X-ray imaging apparatus, said signals caused by X-ray radiation after interaction of said X-ray radiation with an interferometer and with an object to be imaged, said interferometer having an inter-grating distance;
performing, based on the projection data and a forward signal model of a phase contrast signal, a reconstruction operation for one or more images in an image domain of a spatial distribution of at least one physical property of said object including a refractive index, wherein the reconstruction operation is an operation in a phase contrast signal channel with the refractive index as an observable, wherein the reconstruction operation includes performing a scaling operation based on the inter-grating distance of the interferometer and/or on a distance of a location in said image domain from said interferometer; and
outputting said one or more images.

12. A non-transitory computer readable medium having one or more executable instructions, which, when executed by processor circuitry, cause the processor circuitry to perform a method comprising:
receiving interferometric projection data derived from signals acquired by an X-ray detector of an interferometric X-ray imaging apparatus, said signals caused by X-ray radiation after interaction of said X-ray radiation with an interferometer and with an object to be imaged, said interferometer having an inter-grating distance;
performing, based on the projection data and a forward signal model of a phase contrast signal, a reconstruction operation for one or more images in an image domain of a spatial distribution of at least one physical property of said object including a refractive index, wherein the reconstruction operation is an operation in a phase contrast signal channel with the refractive index as an observable, wherein the reconstruction operation includes performing a scaling operation based on the inter-grating distance of the interferometer and/or on a distance of a location in said image domain from said interferometer; and
outputting said one or more images.

* * * * *